United States Patent [19]

Huse

[11] Patent Number: 4,829,607

[45] Date of Patent: May 16, 1989

[54] ISOLATION SYSTEM FOR A SPA

[75] Inventor: Rodger L. Huse, San Luis Obispo, Calif.

[73] Assignee: Donald W. Kern, San Luis Obispo, Calif.

[21] Appl. No.: 181,445

[22] Filed: Apr. 14, 1988

Related U.S. Application Data

[63] Continuation-in-part of Ser. No. 66,095, Jun. 25, 1987, abandoned.

[51] Int. Cl.$^4$ .............................................. A61H 33/02
[52] U.S. Cl. ................................ 4/542; 261/DIG. 42; 261/DIG. 75
[58] Field of Search ...................................... 4/541–544; 137/543, 23, 880, 204; 261/DIG. 42, DIG. 75

[56] References Cited

U.S. PATENT DOCUMENTS

| | | | |
|---|---|---|---|
| 740,225 | 9/1903 | Brown | 137/880 |
| 3,234,959 | 2/1966 | Feinberg | 137/543.23 |
| 3,775,314 | 11/1973 | Beitzel et al. | 261/DIG. 75 |
| 4,166,296 | 9/1979 | Darrah et al. | 4/543 |
| 4,548,232 | 10/1985 | Rusteberg | 137/519 |
| 4,640,783 | 2/1987 | Kern | 4/490 |

FOREIGN PATENT DOCUMENTS 2534471  10/1982  France ................................. 4/541

Primary Examiner—Henry J. Recla
Assistant Examiner—Linda J. Sholl
Attorney, Agent, or Firm—Gordon L. Peterson; Loyal M. Hanson

[57] ABSTRACT

A system for supplying sanitizing gas to a spa includes a sanitizing gas generator for generating sanitizing gas, a conduit for conducting the sanitizing gas from the generator to the spa, and an isolation device coupled to the conduit between the spa and the generator. An arrangement for creating subatmospheric suction pressure in at least a region of the conduit is employed whereby the isolation device is subjected to said suction pressure and the sanitizing gas is caused to flow from the generator to the spa. The isolation device has a drain opening through which liquid can flow to protect the generator from a backflow of water from the spa and a valve responsive to said suction pressure to seal said outlet port sufficiently to prevent significant loss of the suction pressure and of the sanitizing gas when the subatmospheric suction pressure is present. The valve may include a valve seat, a valve element, and a spring for spring biasing the valve element toward the valve seat so that the suction pressure draws the valve element against the valve seat to close the valve.

10 Claims, 1 Drawing Sheet

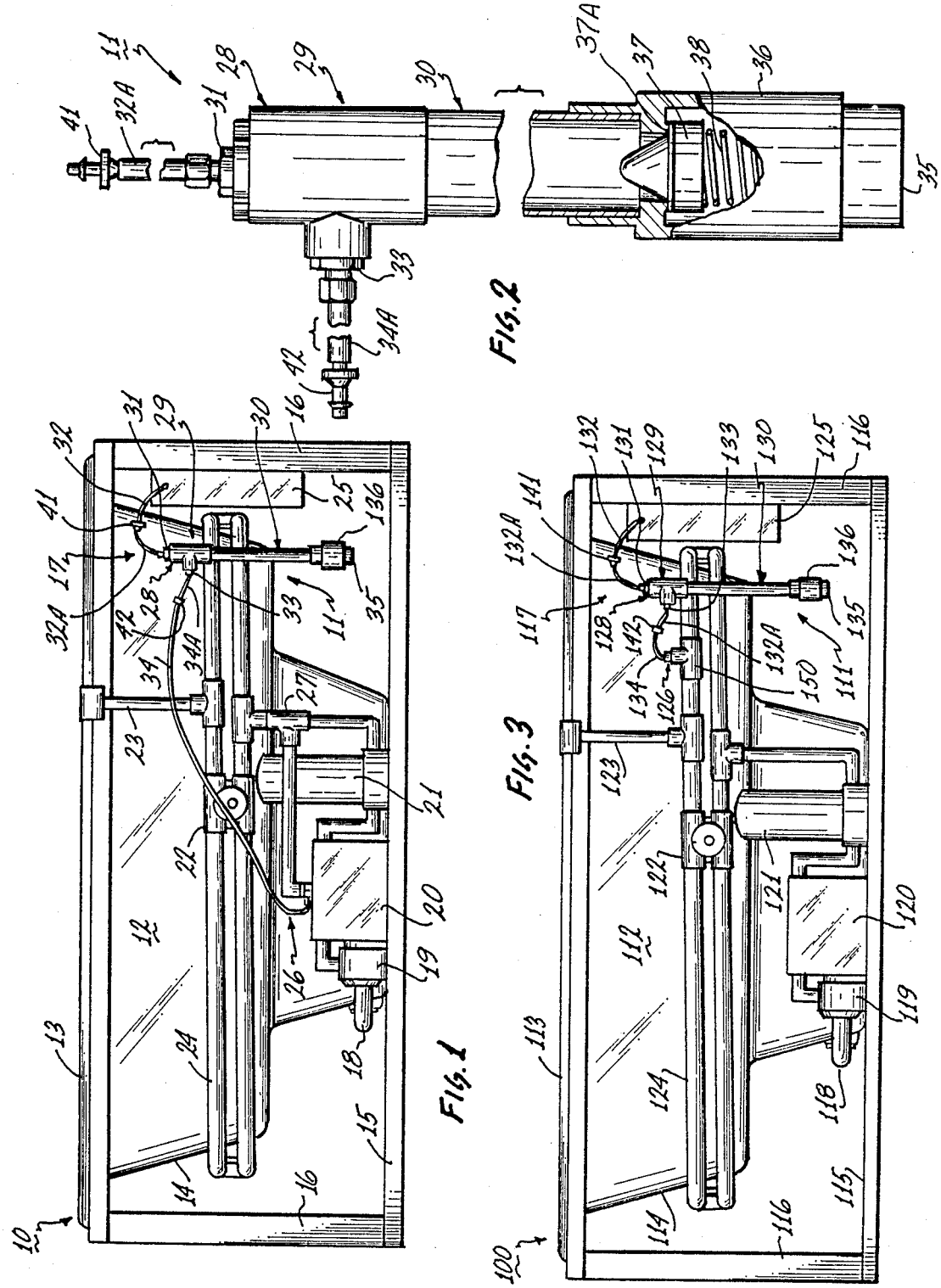

ISOLATION SYSTEM FOR A SPA

CROSS REFERENCE TO RELATED APPLICATION

This application is a continuation in part of U.S. patent application Ser. No. 066,095 filed June 25, 1987, now abandoned, entitled "Isolation System For A Spa" that names the same inventor as this application.

BACKGROUND OF THE INVENTION

1. Technical Field

The invention relates generally to the sanitation of water in swimming pools and spas, and more particularly to an apparatus for use in isolating a source of sanitizing gas from the water being sanitized.

2. Background Information

Sanitizing water, in a spa for example, by the introduction of a sanitizing gas, such as ozone, serves to kill harmful microorganisms. It may be accomplished by generating the sanitizing gas as needed with an electrically powered generator, such as a conventional ozone generator, and coupling gas from this source over a supply line to the spa. For this purpose, gas bubbles may be entrained in a liquid pumped through a venturi to the spa in the manner described in U.S. Pat. No. 4,640,783 to Kern.

In doing this, it is important to guard against the passage of liquid back to the source where it might damage the generator or create a hazardous conductive path to the electrical power. In this regard, related Underwriter Laboratories specifications require the generator to be above the water level in the spa, and existing generators may be mounted at a point five feet removed from the spa for this purpose. With this technique, the relative height of the generator inhibits passage of liquid through the supply line back to the generator, and the distance of the generator from the spa limits exposure to water that may splash from the spa.

However, this arrangement involves the added cost and inconvenience of running lines to the generator and associated equipment. It may also be somewhat unattractive. Consequently, it is desirable to have a new and improved isolation system for a spa that alleviates these concerns—one that need not be located remote from and above the level of the spa.

A typical sanitizing gas generator, such as an ozone generator, simply provides the sanitizing gas, but does not provide it under pressure that would propel the gas from the generator to the desired location for utilization. Accordingly, as suggested by Kern U.S. Pat. No. 4,640,783, the sanitizing gas generator can advantageously be coupled to a suction line leading to the usual plumbing system for the pool or spa.

The suction line is under subatmospheric pressure, and the subatmospheric pressure may be created, for example, by pumping water or air through a venturi and coupling the sanitizing gas generator and the associated suction conduit to the throat of the venturi. The subatmospheric pressure at the throat of the venturi resulting from passage of the fluid through the venturi creates suction in the suction line sufficient to draw the sanitizing gas from the generator to the venturi where it is entrained in the water or air stream passing through the venturi.

Darrah, et al., U.S. Pat. No. 4,166,296, discloses a pressurized air supply system for a spa which includes an air blower for forcing air under pressure to the spa and a float valve between the air blower and the spa for draining water that may leak back to the float valve. This system is not usable in a vacuum or suction system for sanitizing gas because the suction would lift the float valve off of its seat and allow the escape of the suction pressure and the sanitizing gas.

SUMMARY OF THE INVENTION

This invention recognizes the problems associated with the prior art and provides a new and improved isolation system with the desired attributes.

Briefly, the above and further objects of the present invention are realized by providing an apparatus that is inserted in the supply line through which a sanitizing gas is coupled to the spa. It functions to discharge any liquid passing back through the supply line toward the source of gas, to thereby isolate the source, and it responds to subatmospheric pressure in the supply line to limit loss of, and preferably essentially prevent loss of, the sanitizing gas.

Generally, a system for supplying sanitizing gas to a spa includes a sanitizing gas generator for generating sanitizing gas, a conduit for conducting the sanitizing gas from the generator to the spa, and an isolation device coupled to the conduit between the spa and the generator.

An arrangement for creating subatmospheric suction pressure in at least a region of the conduit is employed whereby the isolation device is subjected to said suction pressure and the sanitizing gas is caused to flow from the generator to the spa.

The isolation device has a discharge port through which liquid can flow to protect the generator from a backflow of water from the spa and a valve responsive to said suction pressure to seal the discharge port sufficiently to prevent significant loss of the suction pressure and of the sanitizing gas when the subatmospheric suction pressure is present.

The valve may include a valve seat, a valve element, and a spring for spring biasing the valve element toward the valve seat. The spring preferably creates a force against the valve element which is only slightly greater than the weight of the valve element so that the spring can hold the valve element very lightly against the valve seat.

As such, the spring locates the valve element but does not apply a strong closing force. Rather, the suction pressure draws the valve element against the valve seat to seal and fully close the valve. If a stronger spring were employed, it would take a higher column of water acting against the valve element to open it, and this would either unnecessarily increase the size of the isolation system and/or increase the likelihood that the valve would not open soon enough to protect the sanitizing gas generator.

Thus, this invention utilizes the suction pressure, which is inherently present in a system of this kind, to at least assist in sealing the isolation system against significant loss of the subatmospheric pressure and the sanitizing gas.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 1 of the drawings is a schematized elevation view of a spa employing a system constructed according to the invention;

FIG. 2 is an enlarged detail of the isolation apparatus, shown foreshortened with portions in cross section; and FIG. 3 is a schematized view similar to FIG. 1 of another embodiment in which the sanitizing gas is introduced into an air line.

DESCRIPTION OF THE PREFERRED EMBODIMENTS

Referring now to FIG. 1, there is shown a spa 10 employing an isolation device or apparatus 11 constructed according to the invention. The spa 10 includes a tub 12 having an upper rim 13 circumscribing a tub body 14. The tub body 14 is set atop a base 15, and a skirt 16 extends generally from the upper rim 13 to the base 15 to define an enclosed space 17. The skirt 16 extends substantially fully around the tub body 14 so that the enclosed space is relatively inaccessible by users of the spa 10 and protected from water splashing from the tub 11.

Water from the spa 10 is recirculated conventionally, passing through a suction line 18, pump 19, heater 20, and filter 21, for reintroduction into the tub 12 through jets 22 (only one jet 22 being shown in FIG. 1), along with air received through a vent 23 that passes through an air line 24 to the jet 22.

A source of sanitizing air or ozone generator 25 is mounted within the enclosed space 17, along with the isolation apparatus 11. The generator 25 conventionally produces ozone at a pressure essentially no greater than atmospheric, which is typically atmospheric. The generator 25 is coupled through a supply line 26 that functions as conduit means for conducting the sanitizing gas from the generator to a venturi 27 in the spa 10. The venturi 27 produces a subatmospheric pressure in the supply line 26, while ozone bubbles are entrained by the water flowing from the filter 21 back to the tub 12 that serve to kill microorganisms in the water and thereby sanitize the water. Thus, the venturi 27 functions as means for creating subatmospheric suction pressure in at least a region of the supply line 26 (the conduit means) whereby the isolation apparatus 11 is subjected to the suction pressure and the sanitizing gas is caused to flow from the generator 25 to the spa 10.

The isolation apparatus 11 includes a fitting 28 that is interposed in the supply line 26 between the generator 25 and the venturi 27. The fitting 28 has an upper portion 29 and a lower portion 30, and it is adapted to be mounted with the upper portion 29 disposed higher than the lower portion 30. The fitting 28 may be mounted by suitable means in this position, and doing so results in the discharge of water under influence of gravity as subsequently described. Mounting of the fitting 28 may be accomplished as illustrated, by using the supply line 26 as a support.

The isolation apparatus 11 includes an inlet port 31 in the upper portion 29 of the fitting 28 through which to couple the sanitizing gas or ozone from the generator 25 to the fitting 28. A section 32 of the supply line 26 couples the ozone in this manner.

The isolation apparatus 11 includes an outlet port 33 in the upper portion 29 of the fitting 28 that is in fluid communication with the inlet port 31 through which to couple the ozone from the fitting 28 to the spa 10. A section 34 of the supply line 26 couples the ozone to the venturi 27 for this purpose.

The isolation apparatus 11 includes a discharge port 35 in the lower portion 30 of the fitting 28 through which to discharge under the influence of gravity any liquid flowing into the fitting 28 through the outlet port 33 in order to inhibit passage of the liquid through the inlet port 31 toward the generator 25. The discharge port 35 is in fluid communication with a passage defined by the fitting 28 that extends to the outlet port 33.

A water evacuation valve or valve 36 slightly upstream from the discharge port 35 serves as means for inhibiting passage of the sanitizing gas through the discharge port 35 while enabling passage of the liquid. The valve 36 includes a valve element 37, valve seat 37A, and spring 38 (FIG. 2), and the spring 38 functions as spring biasing means for urging the valve element 37 lightly into engagement with the valve seat 37A so that the suction pressure draws the valve element 37 tightly against the valve seat 37A to seal the valve 36.

This retains the valve 36 in a normally closed condition when fluid is flowing in the venturi 27, i.e., the spa 10 is turned on, to create suction pressure in line 26. When no fluid is flowing in the venturi 27, i.e., when the spa is turned off, a predetermined low level of liquid in the discharge passage is sufficient to overcome the light force of the spring 38 to open the valve 36. The valve 36 functions as valve means responsive to the suction pressure to seal the discharge port 35 sufficiently to prevent significant loss of the suction pressure and of the sanitizing gas when the subatmospheric suction pressure is present.

It should be understood that the only period during which there is danger of water from the tub 12 backflowing toward the ozone generator 25 is when the spa is turned off, i.e., when there is no water flowing through the venturi 27 to the tub 12. During this time it is possible for water from the tub 12 to backflow toward the ozone generator 25. However, if this occurs, there is no vacuum pressure to hold the valve element 37 tightly shut and accordingly, the valve can be easily opened by a low static head of water acting against it. Conversely, when the valve element 37 is sealed or essentially sealed against the valve seat 37A, there is no danger of water backflowing to the ozone generator and so the fact that the valve 36 is held tightly shut to prevent the loss of ozone and the loss of vacuum pressure, poses no threat to the ozone generator 25.

These and other details of the isolation apparatus 11 are further illustrated in FIG. 2. The fitting 28 may employ PVC components, the upper portion 29 being a conventional PVC T-connector and the lower portion 30 being a length of conventional PVC tubing. With this arrangement, the interior of the PVC tubing constitutes a first portion of the passage extending between the discharge port 35 and the outlet port 33, and the valve 36 constitutes a second portion.

Preferably the PVC tubing has a cross sectional area substantially greater than that of the supply line 26 and, therefore the outlet port 33, and may be as much as twenty times greater. This results in sufficient water pressure to activate the valve 36 without employing an excessively long length of PVC tubing.

The spring 38 may be chosen so that approximately one-third pound of pressure is sufficient to activate the valve 36 when the suction is off. Thus, with the suction off, if any water accumulates in the lower portion 30 of the fitting 28 to a predetermined level resulting in this amount of pressure, the valve 36 opens to evacuate the water. Otherwise, the spring 38 retains the valve element 37 sufficiently close to the valve seat 37A that the subatmospheric pressure retains the valve 36 sealed, thereby inhibiting passage of the sanitizing gas out of the discharge port 35.

To further inhibit a backflow of water, i.e. water flowing through the supply line 26 toward the generator 25, the fitting 28 may include a first check valve 41 that is coupled to the inlet port 31 by a length of tubing 32A and to the first section 32 of the supply line 26, along with a second check valve 42 that is coupled to the outlet port 33 by a length of tubing 34A and to the second section 34. These valves are oriented to pass ozone flowing toward the spa 10 while inhibiting liquid flowing toward the generator 25.

A second embodiment of a spa, a spa 110, that utilizes an isolation apparatus 111 constructed according to the invention is illustrated in FIG. 3. For convenience, many reference numerals in FIG. 3 are increased by one hundred over those designating similar features in FIG. 1, and the similar components so designated are not further described.

In the spa 110, the supply line 126 couples the ozone from the generator 125 to a venturi 150 (the counterpart of the venturi 27 in FIG. 1) in the air line 124. This arrangement also creates suction pressure in the line 126 and achieves introduction of the ozone through a jet 122 and isolation of the ozone generator 125 in the same manner as described above in connection with FIG. 1.

Thus, this invention provides a new and improved isolation apparatus that overcomes many problems associated with existing techniques and enables the apparatus, source, and associated equipment to all be conveniently located next to the spa, behind the skirt. Although an exemplary embodiment of the invention has been shown and described, many changes, modifications, and substitutions may be made by one having ordinary skill in the art without necessarily departing from the spirit and scope of this invention.

What is claimed is:

1. A system for supplying sanitizing gas to a spa comprising:
    a sanitizing gas generator for generating sanitizing gas;
    conduit means for conducting the sanitizing gas from the generator to the spa;
    an isolation device coupled to the conduit between the spa and the generator; and
    means for creating subatmospheric suction pressure in at least a region of the conduit means whereby the isolation device is subjected to said suction pressure and the sanitizing gas is caused to flow from the generator to the spa;
    said isolation device having a discharge port through which liquid can flow to protect the generator from a backflow of water from the spa; and
    said isolation device including valve means responsive to said suction pressure to seal said discharge port sufficiently to prevent significant loss of the suction pressure an of the sanitizing gas when said means for creating subatmospheric suction pressure is operating.

2. A system as recited in claim 1, wherein the valve means includes:
    a valve seat;
    a valve element; and
    means for spring biasing the valve element toward the valve seat so that the suction pressure draws the valve element against the valve seat to substantially seal the valve means.

3. A system as recited in claim 1, wherein the isolation device includes:
    a fitting having an upper portion and a lower portion, which fitting is adapted to be mounted with the upper portion disposed higher than the lower portion;
    an inlet port in the upper portion of the fitting through which to couple the sanitizing gas from the sanitizing gas generator to the fitting;
    an outlet port in the upper portion of the fitting that is in fluid communication with the inlet port through which to couple the sanitizing gas from the fitting to the spa;
    a discharge port in the lower portion of the fitting through which to discharge under the influence of gravity any liquid flowing into the fitting through the drain opening order to inhibit passage of the liquid through the inlet port toward the source, which discharge port is in fluid communication with a passage defined by the fitting that extends to the drain opening; and
    valve means for inhibiting passage of the sanitizing gas through the discharge port while enabling passage of the liquid, which valve means includes a valve element, a valve seat, and spring biasing means for biasing the valve element toward the valve seat when there is less than a predetermined level of the liquid in the discharge passage while enabling the valve means to open under pressure presented by the liquid when the level of the liquid rises to the predetermined level.

4. An apparatus as recited in claim 3, wherein:
    the predetermined level is below the inlet port.

5. An apparatus as recited in claim 3, wherein:
    the predetermined level is below the outlet port.

6. An apparatus as recited in claim 5, wherein:
    the outlet port is disposed below the inlet port.

7. An apparatus as recited in claim 3, wherein:
    the discharge passage has a cross sectional area substantially larger than the cross sectional area of the outlet port.

8. An apparatus as recited in claim 3, further comprising:
    first check valve means coupled to the inlet port for inhibiting fluid flow from the fitting toward a source of sanitizing gas with which the fitting is used; and
    second check valve means coupled to the outlet port for inhibiting fluid flow toward the fitting from a spa with which the fitting is used.

9. A system as recited in claim 1, wherein the isolation device includes:
    a fitting having an upper portion and a lower portion, which fitting is adapted to be mounted within the enclosed space so that the upper portion is disposed higher than the lower portion;
    an inlet port in the upper portion of the fitting through which to couple the sanitizing gas from the source to the fitting;
    an outlet port in the upper portion of the fitting that is in fluid communication with the inlet port through which to couple the sanitizing gas from the fitting to the spa;

a discharge port in the lower portion of the fitting through which to discharge under the influence of gravity any liquid flowing into the fitting through the outlet port in order to inhibit passage of the liquid through the inlet port toward the source, which discharge port is in fluid communication with a passage defined by the fitting that extends to the outlet port; and valve means for inhibiting passage of the sanitizing gas through the discharge port while enabling passage of the liquid, which valve means includes a valve element, a valve seat, and spring biasing means for retaining the valve element toward the valve seat when there is less than a predetermined level of the liquid in the discharge passage while enabling the valve means to open under pressure presented by the liquid when the level of the liquid rises to the predetermined level.

10. A system as recited in claim 1, wherein:
the sanitizing gas generator generates sanitizing gas at a pressure which is essentially no greater than atmospheric.

* * * * *